US011547510B2

(12) United States Patent
Bassik

(10) Patent No.: US 11,547,510 B2
(45) Date of Patent: Jan. 10, 2023

(54) EVENT INITIATED RELEASE OF FUNCTION SELECTION CONTROL FOR ROBOTIC SURGICAL SYSTEMS

(71) Applicant: Covidien LP, Mansfield, MA (US)

(72) Inventor: Renen Bassik, Brookline, MA (US)

(73) Assignee: COVIDIEN LP, Mansfield, MA (US)

( * ) Notice: Subject to any disclaimer, the term of this patent is extended or adjusted under 35 U.S.C. 154(b) by 667 days.

(21) Appl. No.: 16/614,926

(22) PCT Filed: May 17, 2018

(86) PCT No.: PCT/US2018/033097
§ 371 (c)(1),
(2) Date: Nov. 19, 2019

(87) PCT Pub. No.: WO2018/217527
PCT Pub. Date: Nov. 29, 2018

(65) Prior Publication Data
US 2020/0170737 A1    Jun. 4, 2020

Related U.S. Application Data

(60) Provisional application No. 62/510,802, filed on May 25, 2017.

(51) Int. Cl.
*A61B 34/30* (2016.01)
*A61B 34/00* (2016.01)
(Continued)

(52) U.S. Cl.
CPC .............. *A61B 34/74* (2016.02); *A61B 18/12* (2013.01); *A61B 34/25* (2016.02); *A61B 34/37* (2016.02);
(Continued)

(58) Field of Classification Search
CPC ......... A61B 34/74; A61B 34/70; A61B 34/37; A61B 34/25; A61B 2090/0807;
(Continued)

(56) References Cited

U.S. PATENT DOCUMENTS 7,270,664 B2 * 9/2007 Johnson ............. A61B 18/1445
606/45
8,828,023 B2 * 9/2014 Neff ....................... A61B 34/37
606/130
(Continued)

FOREIGN PATENT DOCUMENTS

JP     2012513845 A    6/2012
JP     2014523277 A    9/2014
(Continued)

OTHER PUBLICATIONS

Japanese Office Action dated Jan. 25, 2022 corresponding to counterpart Patent Application JP 2019-564877.
(Continued)

*Primary Examiner* — Michael F Peffley
(74) *Attorney, Agent, or Firm* — Carter, DeLuca & Farrell, LLP

(57) ABSTRACT

A method of controlling a function of a surgical instrument of a surgical robot with a input of a user interface includes selecting a function of a surgical instrument to link a input of the user interface with the function of the surgical instrument, actuating the input to activate the function of the surgical instrument, and delinking the input from the surgical instrument in response to an event of the surgical robot or the user interface.

20 Claims, 4 Drawing Sheets

(51) Int. Cl.
  *A61B 34/37* (2016.01)
  *A61B 18/12* (2006.01)
  *A61B 18/00* (2006.01)
(52) U.S. Cl.
  CPC .............. *A61B 2018/0063* (2013.01); *A61B 2018/00601* (2013.01); *A61B 2018/00952* (2013.01); *A61B 2018/00958* (2013.01)
(58) Field of Classification Search
  CPC .......... A61B 18/12; A61B 2017/00017; A61B 2017/00115; A61B 2017/00393; A61B 2017/00973; A61B 2018/00602; A61B 2018/0063; A61B 2018/00952; A61B 2018/00958
  See application file for complete search history.

(56) References Cited

U.S. PATENT DOCUMENTS

| | | |
|---|---|---|
| 2007/0102473 A1 | 5/2007 | Shelton et al. |
| 2009/0030428 A1* | 1/2009 | Omori .................... A61B 34/70 606/130 |
| 2011/0238010 A1* | 9/2011 | Kirschenman .... A61M 25/0105 604/95.04 |
| 2013/0304066 A1 | 11/2013 | Kerr et al. |
| 2014/0005682 A1 | 1/2014 | Worrell et al. |
| 2015/0173849 A1* | 6/2015 | Robinson ............... A61B 34/25 700/257 |

FOREIGN PATENT DOCUMENTS

| | | |
|---|---|---|
| WO | 2010078344 A1 | 7/2010 |
| WO | 2012170256 A1 | 12/2012 |
| WO | 2017053363 A1 | 3/2017 |

OTHER PUBLICATIONS

Japanese Office Action dated Aug. 12, 2022 corresponding to counterpart Patent Application JP 2019-564877.
International Search Report dated Nov. 7, 2018 and Written Opinion completed Nov. 5, 2018 corresponding to counterpart Int'l Patent Application PCT/US2018/033097.
Chinese First Office Action dated Aug. 3, 2022 corresponding to counterpart Patent Application CN 2018800337914.

* cited by examiner

EVENT INITIATED RELEASE OF FUNCTION SELECTION CONTROL FOR ROBOTIC SURGICAL SYSTEMS

CROSS-REFERENCE TO RELATED APPLICATIONS

This application is a National Stage Application of PCT/US2018/033097, filed May 17, 2018 under 35USC § 371 (a), which claims benefit of and priority to U.S. Provisional Patent Application Ser. No. 62/510,802 filed May 25, 2017, the disclosures of each of the above-identified applications are hereby incorporated by reference in their entirety.

BACKGROUND

Robotic surgical systems have been used in minimally invasive medical procedures. During such a medical procedure, the robotic surgical system is controlled by a surgeon interfacing with a user interface. The user interface allows the surgeon to manipulate a surgical instrument that acts on a patient. The user interface includes a handle or gimbal that is moveable by the surgeon to control the robotic system. In some instances, an input of the user interface controls a function of a surgical instrument associated with one of the handles such as clamping of jaws, firing fasteners, firing a knife, delivering electrosurgical energy, etc. The input can be a foot pedal, a trigger, a button, or another suitable input.

During a medical procedure surgical instruments associated with each handle can be swapped such that it may be difficult to know which function is linked with a particular input. In addition, after a period of time has elapsed, a surgeon may not realize that a function is still linked with an input such that a function of the surgical instrument is inadvertently activated.

There is a continuing need for improved linking, safeguards, and control of inputs with surgical instruments of robotic surgical systems.

SUMMARY

The present disclosure relates generally to event initiated release of a function selection control in robotic surgical systems for improving linking and control of inputs with surgical instruments of robotic surgical systems.

In an aspect of the present disclosure, a method of controlling a function of a surgical instrument of a surgical robot with a input of a user interface includes selecting a function of a surgical instrument to link a input of the user interface with the function of the surgical instrument, actuating the input to activate the function of the surgical instrument, and delinking the input from the surgical instrument in response to an event of the surgical robot or the user interface. The input can be a foot pedal.

In aspects, selecting a function of the surgical instrument includes actuating a selection control of the user interface to a desired position. The selection control can be disposed on an input handle of the user interface. Actuating the selection control of the user interface to a desired position includes rotating the selection control to the desired position. The desired position can be cut, bipolar, or seal.

In some aspects, the method includes un-assigning or de-assigning the input handle from a linkage that supports the surgical instrument to delink the input from surgical instrument. Delinking the input from the surgical instrument may include automatically resetting the selection control to an unactuated position.

In particular aspects, the method includes decoupling the surgical instrument from a linkage of the surgical robot which affects delinking the input from the surgical instrument.

In certain aspects, delinking the input from the surgical instrument occurs after a first predetermined amount of time elapses after selecting a function of the surgical instrument. The method may include resetting the first predetermined amount of time after each actuation of the input. The method may include delinking the input from the surgical instrument after a second predetermined amount of time elapses after an actuation of the input and resetting the second predetermined amount of time after each actuation of the input. The first predetermined amount of time may be in a range of about 10 seconds to about 60 seconds. The second predetermined amount of time may be in a range of about 10 seconds to about 60 seconds. The first and second predetermined amounts of time can be the same or different from one another.

In another aspect of the present disclosure, an input handle for a user interface of a robotic surgical system includes a body and a selection control disposed on the body. The selection control is configured to link a function of a surgical instrument associated with a linkage of a robot arm assigned to the input handle to an input. The selection control is configured to reset to an unactuated position in response to an event of the surgical robot.

In aspects, the selection control includes a null position and at least one of a cut position, a bipolar position, and a seal position. The selection control may be biased to the null position.

In some aspects, the selection control provides visual indicia when an input is linked to the input handle to control a function of a surgical instrument associated with a linkage of a robot arm. The selection control may be backlit to provide the visual indicia. For example, the selection control may be backlit in green when an input is linked to the input handle and may be backlit in red when an input is not linked to the input handle.

Further details and aspects of exemplary embodiments of the present disclosure are described in more detail below with reference to the appended figures.

BRIEF DESCRIPTION OF THE DRAWINGS

Various aspects of the present disclosure are described hereinbelow with reference to the drawings, which are incorporated in and constitute a part of this specification, wherein.

DETAILED DESCRIPTION

Figure 1:
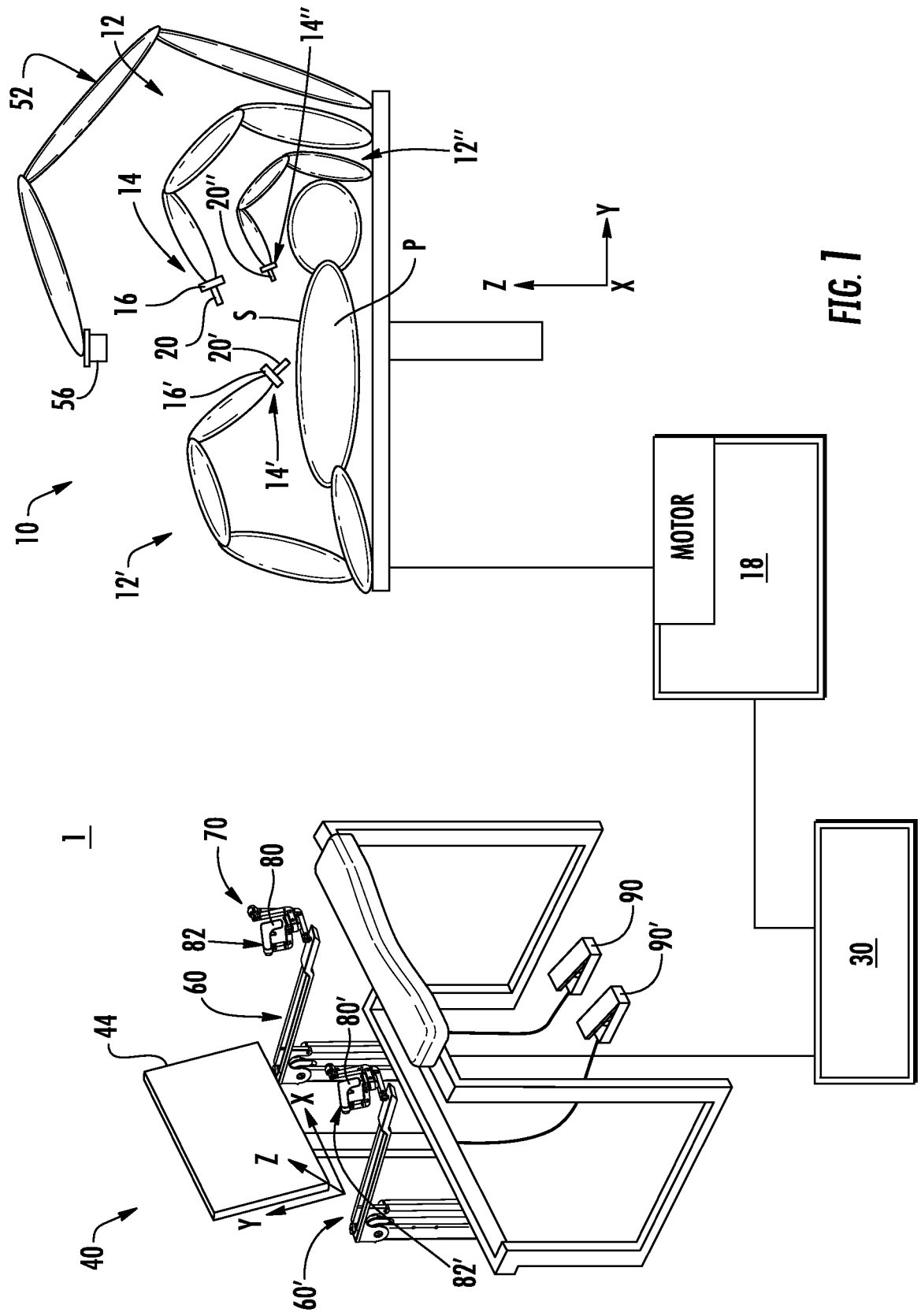
FIG. 1 is a schematic illustration of a user interface and a robotic system in accordance with the present disclosure.

Embodiments of the present disclosure are now described in detail with reference to the drawings in which like reference numerals designate identical or corresponding elements in each of the several views. As used herein, the term "clinician" refers to a doctor, a nurse, a staff member, or any other care provider and may include support personnel. Throughout this description, the term "proximal" refers to the portion of the device or component thereof that is closest to the clinician and the term "distal" refers to the portion of the device or component thereof that is farthest from the clinician.

The present disclosure relates generally to event initiated release of a function selection control in robotic surgical systems for improving linking and control of inputs with surgical instruments of robotic surgical systems. The selection control can be a mechanical switch on an input handle that is biased to a null or unactuated position. The selection control returns to the null position after an event of the robotic surgical system occurs. The event can be passing of a predetermined amount of time, deassignment of a linkage from an input handle, decoupling of a surgical instrument from a linkage, etc.

Referring to FIG. 1, a robotic surgical system 1 is shown generally as a surgical robot 10, a processing unit 30, and a user interface 40. The surgical robot 10 generally includes linkages 12, 12', 12" and a robot base 18. The linkages 12, 12', 12" moveably support surgical instruments or tools 20, 20', 20" which are configured to act on tissue. The linkages 12, 12', 12" may be in the form of arms each having an end 14 that supports a surgical instrument or tool 20, 20', 20" which is configured to act on tissue. In addition, the ends 14 of the linkages 12, 12', 12" may include an imaging device 16 for imaging a surgical site "S". The ends 14 of the linkages 12, 12', 12" may include a tool detection system that identifies a type of surgical instrument supported or attached to the end 14, 14', 14" of the linkage 12, 12', 12". The user interface 40 is in communication with robot base 18 through the processing unit 30.

The user interface 40 includes a display device 44 which is configured to display images of the surgical site "S" which may include data captured by imaging devices 16 positioned on the ends 14 of the linkages 12, 12', 12" and/or include data captured by imaging devices that are positioned about the surgical theater (e.g., an imaging device positioned within the surgical site "S", an imaging device positioned adjacent the patient "P", imaging device 56 positioned at a distal end of an imaging arm 52). The imaging devices (e.g., imaging devices 16, 56) may capture visual images, infrared images, ultrasound images, X-ray images, thermal images, and/or any other known real-time images of the surgical site "S". The imaging devices transmit captured imaging data to the processing unit 30 which creates images (e.g., three-dimensional images) of the surgical site "S" in real-time from the imaging data and transmits the images to the display device 44 for display.

The user interface 40 also includes control arms 60, 60' that support input handles 80, 80' attached to gimbals 70 which allow a clinician to manipulate the robotic system 10 (e.g., move the linkages 12, 12', 12", the ends 14 of the linkages 12, 12', 12", and/or the surgical instruments 20, 20', 20"). Each of the gimbals 70 is in communication with the processing unit 30 to transmit control signals thereto and to receive feedback signals therefrom. Additionally or alternatively, each of the input handles 80, 80' may include control interfaces which allow the surgeon to actuate (e.g., clamp, grasp, fire, open, close, rotate, thrust, slice, etc.) the surgical instruments 20, 20', 20" supported at the ends 14 of the linkages 12, 12', 12". The user interface 40 further includes foot pedals 90, 90' that may be used with one or both of the input handles 80, 80' to activate functions of the surgical instruments 20, 20', 20".

Each of the gimbals 70 is moveable to move the ends 14 of the linkages 12, 12', 12" within a surgical site "S". The three-dimensional images on the display device 44 are orientated such that movement of the gimbals 70 moves the ends 14 of the linkages 12, 12', 12" as viewed on the display device 44. It will be appreciated that the orientation of the three-dimensional images on the display device 44 may be mirrored or rotated relative to view from above the patient "P". In addition, it will be appreciated that the size of the three-dimensional images on the display device 44 may be scaled to be larger or smaller than the actual structures of the surgical site "S" permitting the surgeon to have a better view of structures within the surgical site "S". As the gimbal 70 is moved, the surgical instruments 20, 20', 20" are moved within the surgical site "S". Movement of the surgical instruments 20, 20', 20" may also include movement of the ends 14 of the linkages 12, 12', 12" which support the surgical instruments 20, 20', 20".

For a detailed discussion of the construction and operation of a robotic surgical system 1, reference may be made to U.S. Pat. No. 8,828,023, the entire contents of which are incorporated herein by reference.

Figure 2:
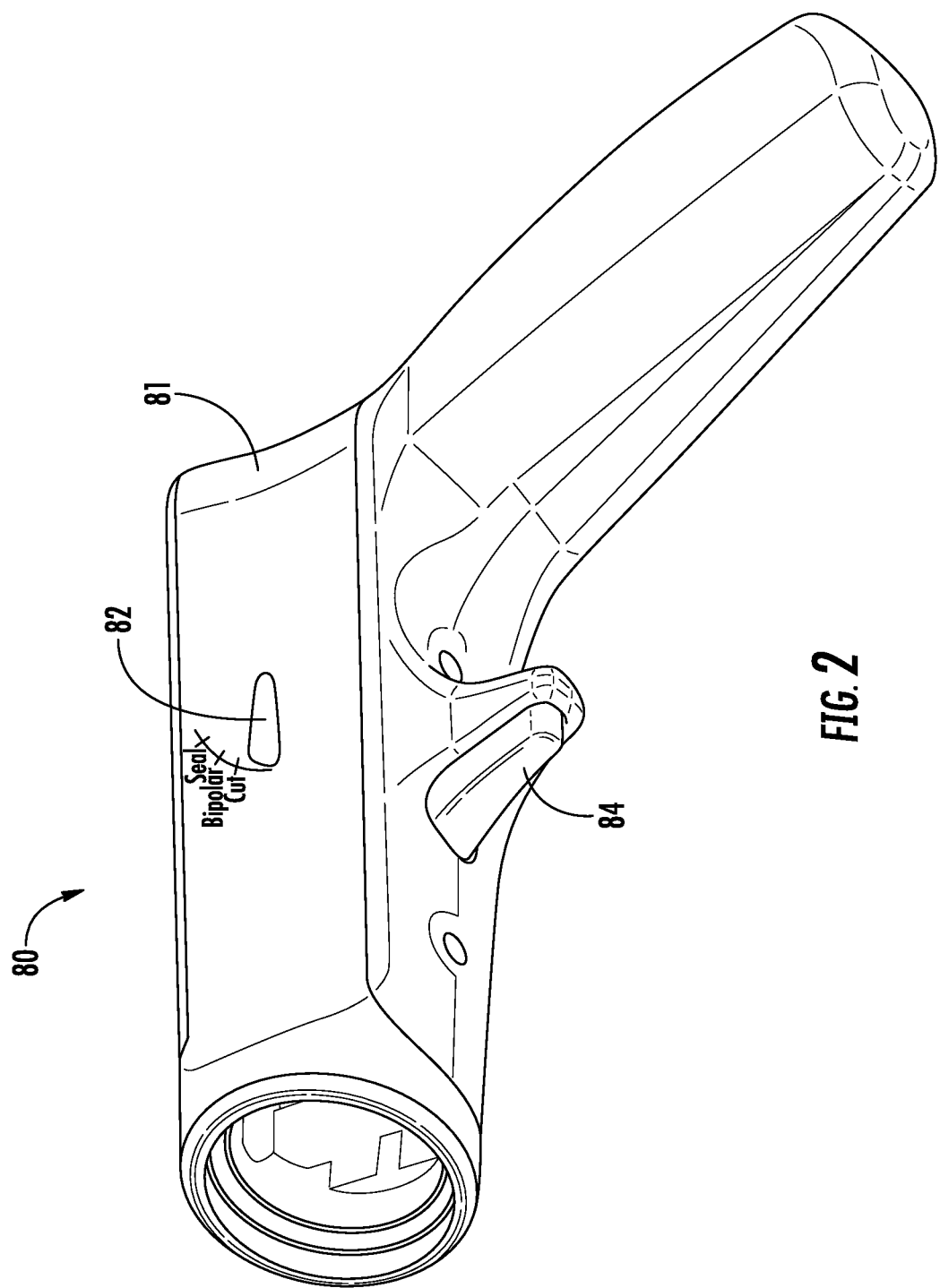
FIG. 2 is an enlarged perspective view of an input handle of the user interface of FIG. 1.
Figure 3:
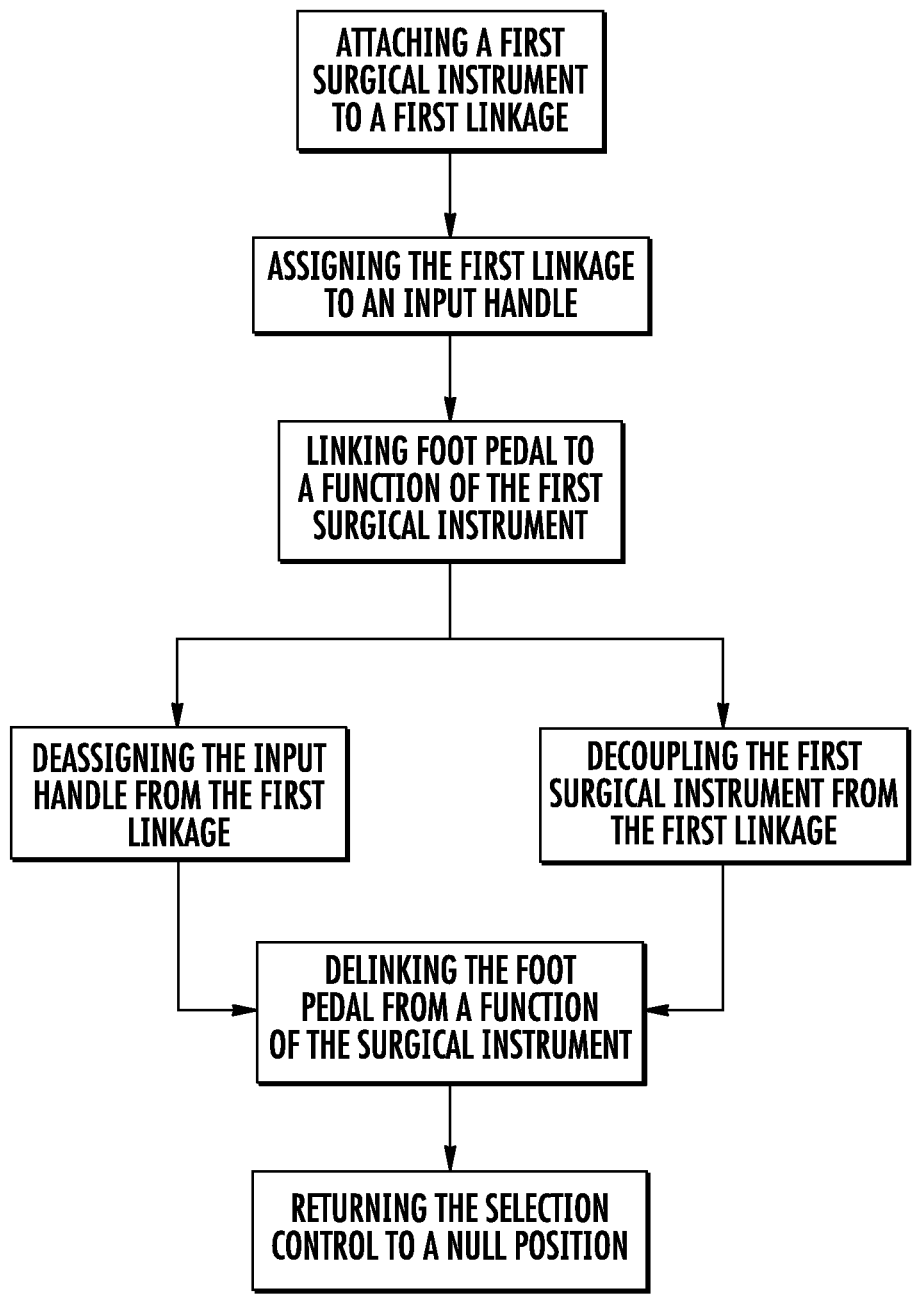
FIG. 3 is a flowchart illustrating a method of event initiated release of a function selection control for a robotic surgical system.
Figure 4:
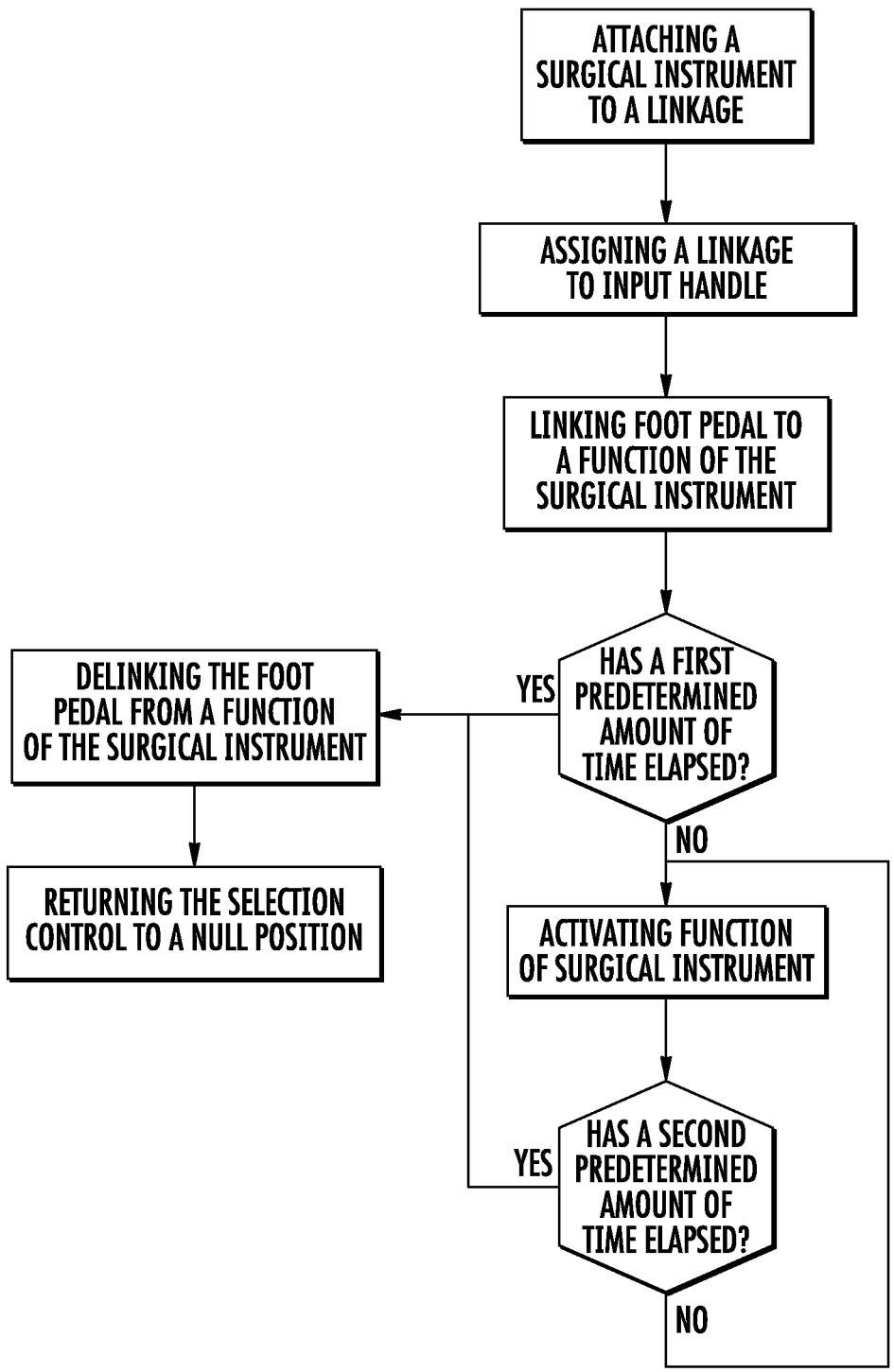
FIG. 4 is a flowchart illustrating another method of event initiated release of a function selection control for a robotic surgical system.

Referring now to FIG. 2, the input handle 80 is shown in accordance with the present disclosure. It is envisioned that the input handle 80 may take a plurality of shapes and sizes. Further, the input handle 80 can include control elements unique to a surgical instrument 20 assigned with the input handle 80. It is envisioned that although the input handles 80 and 80' may have different control interfaces, that the input handles 80 and 80' function in a substantially similar manner which will be described with respect to input handle 80 below.

The input handle 80 has a body 81 that includes a selection control 82 and an activation control 84. The selection control 82 links the foot pedal 90 (FIG. 1) with a surgical instrument (e.g., surgical instrument 20, 20', 20") associated with a linkage (e.g., linkage 12, 12', 12") assigned to the input handle 80 such that actuation (e.g., depressing) of the foot pedal 90 activates a function of the linked surgical instrument. For the remainder of this example, the input handle 80 is assigned to linkage 12 and the surgical instrument 20 is coupled to linkage 12 to associate the surgical instrument 20 with the linkage 12.

As shown, the selection control 82 is a rotary mechanical switch with, for example, four positions: an unactuated or null position, a cut position, a bipolar position, and a seal position. It is envisioned that the selection control 82 can have any number of positions and can be a push button switch, a lever switch, a slider switch, a capacitance switch, a proximity sensor, a rotary dial, etc. The selection control 82 is biased to the unactuated or null position. The selection control 82 is actuated to link a function of the surgical instrument 20 associated with the linkage 12 that is assigned to the input handle 80 with the foot pedal 90. For example, as shown, the selection control 82 is rotated to link a function of the surgical instrument 20 associated with the linkage 12 that is assigned to the input handle 80 with the foot pedal 90. After the selection control 82 is actuated to a desired position (e.g., the cut position), the selection control 82 can remain in the desired position while a function of the surgical instrument 20 is linked to the foot pedal 90. The selection control 82 remains in the desired position to provide indicia that the function of the surgical instrument is linked to actuation of the foot pedal 90.

It is contemplated that the selection control 82 can be backlit to provide visual indicia of the linking of the foot pedal 90 with a surgical instrument 20 associated with the input handle 80. For example, when the foot pedal 90 is linked with a function of the surgical instrument 20, the selection control 82 can be backlit green, and when the foot pedal 90 is not linked, the selection control 82 can be backlit red.

During a medical procedure, the assignment of the input handle 80 can be changed from the linkage 12 to the linkage 12' or can be deassigned from all linkages. When the assignment of the input handle 80 is changed, the processing unit 30 delinks the foot pedal 90 from the function of the surgical instrument 20 and sends a feedback signal to the input handle 80 which releases the selection control 82 such that the selection control 82 returns to the null or unactuated position. Additionally or alternatively, the surgical instrument 20, coupled to the assigned linkage 12, can be changed during the medical procedure such that a surgical instrument 20 associated with the input handle 80 is physically changed. In response, the surgical robot 10 sends a feedback signal indicative of the surgical instrument change to the processing unit 30. Further in response, the processing unit 30 delinks the foot pedal 90 from the function of the surgical instrument 20 and sends a feedback signal to the input handle 80 which releases the selection control 82 such that the selection control 82 returns to the null or unactuated position. Delinking the foot pedal 90 from the surgical instrument 20 prevents inadvertent activation of the function of the surgical instrument 20.

In embodiments where the selection control 82 is backlit, the processing unit 30 can send a feedback signal to the input handle 80 to alter the backlighting of the selection control 82 when the foot pedal 90 is delinked from the function of the surgical instrument 20. For example, the backlighting of the selection control 82 can change color, pattern, or intensity in response to the feedback signal to provide visual indicia of the delinking of the foot pedal 90.

Additionally or alternatively, the processing unit 30 may time out the link between the foot pedal 90 and the function of the surgical instrument 20. Specifically, after the foot pedal 90 is linked to a function of the surgical instrument 20 for a predetermined amount of time without the foot pedal 90 activating the function of the surgical instrument 20, the processing unit 30 delinks the foot pedal 90 from the function of the surgical instrument 20 and sends a feedback signal to the input handle 80 which releases the selection control 82 such that the selection control 82 returns to the null or unactuated position. The predetermined amount of time can be reset when the selection control 82 is actuated to link the foot pedal 90 to a function of the surgical instrument 20 associated with the input handle 80 and/or when the foot pedal 90 is actuated to activate the function of the surgical instrument 20. It is contemplated that the predetermined amount of time can have a first predetermined amount of time after linking of the foot pedal 90 to a function of the surgical instrument 20 and a second predetermined amount of time after actuation of the foot pedal 90 to active the function of the surgical instrument 20. The first and second predetermined amounts of time can have the same value in a range of about 10 seconds to about 60 seconds. Alternatively, the first and second predetermined amounts of time can have different values with the first predetermined amount of time in a range of about 10 seconds to about 60 seconds and the second predetermined amount of time in a range of about 10 seconds to about 60 seconds.

Referring now to FIGS. 1-4, methods of controlling a robotic surgical system during a medical procedure are disclosed in accordance with the present disclosure. Initially, a surgical robot similar to the surgical robot 10 detailed above is prepared for the medical procedure. To prepare the surgical robot, clinicians attach or couple surgical instruments to linkages of the surgical robot. For example, the surgical robot may have three linkages with a different surgical instrument coupled to an end of each linkage. A first surgical instrument 20 configured to deliver monopolar electrosurgical energy to tissue and can be coupled to a first linkage 12, a second surgical instrument 20' configured to deliver bipolar electrosurgical energy to tissue and can be coupled to a second linkage 12', and a third surgical instrument 20" configured as a vessel sealer can be coupled to a third linkage 12".

At the user interface 40, a surgeon utilizes the user interface 40 to control the surgical robot 10. The surgeon assigns the left input handle 80' to control the first linkage 12 and assigns the right input handle 80 to control the second linkage 12'. Then the surgeon sets a selection control 82' on the left input handle 80' to cut which links a left foot pedal 90' to the first surgical instrument 20 such that actuation of the left foot pedal 90' delivers monopolar energy to tissue with the first surgical instrument 20. Next, the surgeon sets a selection control 82 on the right input handle 80 to bipolar which links the right foot pedal 90 to the second surgical instrument 20' such that actuation of the right foot pedal 90 delivers bipolar energy to tissue with the second surgical instrument 20'.

During the medical procedure, the surgeon can deassign the left input handle 80' from the first linkage 20. When the processing unit 30 detects an assignment change of the left input handle 80', the processing unit 30 delinks the left foot pedal 90' from the function of the first surgical instrument 20 and sends a feedback signal to the left input handle 80' to reset the selection control 82' to the null or unactuated position. The surgeon can then assign the left input handle 80' to the third linkage 12" and set the selection control 82' to vessel sealing which links the left foot pedal 90' to the third surgical instrument 20" such that actuation of the left foot pedal 90' delivers electrosurgical energy to tissue which is configured to seal vessels.

During the medical procedure, clinicians can decouple the third surgical instrument 20" from the third linkage 12" when the surgical instrument 20" may require cleaning, reaches its end of life, requires replacement, or changing to a new type of instrument, etc. When the surgical instrument 20" is decoupled, the surgical robot 10 sends a feedback signal to the processing unit 30 indicative of the decoupling of the surgical instrument 20". In response to the feedback signal from the surgical robot 10, the processing unit 30 delinks the left foot pedal 90' from the function of the third surgical instrument 20" and sends a feedback signal to the left input handle 80' to move the selection control 82' to the null or unactuated position. The surgeon can then move the selection control 82' back to a desired position appropriate for a surgical instrument coupled to the third linkage 12" which is still assigned to the left input handle 80' to link a function of the surgical instrument to the left foot pedal 90'.

During the medical procedure, after the surgeon links one of the foot pedals (e.g., right or left foot pedal 90, 90') to a respective surgical instrument (e.g., surgical instrument 20, 20', 20"), the processing unit 30 can time out the link between the foot pedal and the function of the respective surgical instrument after a first predetermined amount of time. Additionally or alternatively, the processing unit 30 can time out the link between the foot pedal and the function of the respective surgical instrument after a second predetermined amount of time after an actuation of the respective surgical instrument. The first and second predetermined amount of times can be reset with each actuation of the respective surgical instrument in response to an actuation of the linked foot pedal. The first and second predetermined amounts of time can be the same or the first and second predetermined amounts of time can be different from one another. After the foot pedal is delinked from the respective surgical instrument, the surgeon can relink the foot pedal with the respective surgical instrument as detailed above.

As detailed above, the user interface 40 allows a surgeon to selectively link a foot pedal (e.g., right or left foot pedal 90, 90') to a respective surgical instrument of a surgical robot 10; however, it is envisioned that the user interface 40 can include other inputs such as triggers, buttons, etc. which can be selectively linked to a respective surgical instrument of a surgical robot 10 in a similar manner to the foot pedals detailed above.

As detailed above and shown in FIG. 1, the user interface 40 is in operable communication with the surgical robot 10 to perform a surgical procedure on a patient "P"; however, it is envisioned that the user interface 40 may be in operable communication with a surgical simulator (not shown) to virtually actuate a robot system and/or surgical instrument in a simulated environment. For example, the surgical robot system 1 may have a first mode where the user interface 40 is coupled to actuate the surgical robot 10 and a second mode where the user interface 40 is coupled to the surgical simulator to virtually actuate a robot system. The surgical simulator may be a standalone unit or be integrated into the processing unit 30. The surgical simulator virtually responds to a clinician interfacing with the user interface 40 by providing visual, audible, force, and/or haptic feedback to a clinician through the user interface 40. For example, as a clinician interfaces with the input device handles 80, 80', the surgical simulator moves representative surgical instruments that are virtually acting on tissue at a simulated surgical site. It is envisioned that the surgical simulator may allow a clinician to practice a surgical procedure before performing the surgical procedure on a patient. In addition, the surgical simulator may be used to train a clinician on a surgical procedure. Further, the surgical simulator may simulate "complications" during a proposed surgical procedure to permit a clinician to plan a surgical procedure.

While several embodiments of the disclosure have been shown in the drawings, it is not intended that the disclosure be limited thereto, as it is intended that the disclosure be as broad in scope as the art will allow and that the specification be read likewise. Any combination of the above embodiments is also envisioned and is within the scope of the appended claims. Therefore, the above description should not be construed as limiting, but merely as exemplifications of particular embodiments. Those skilled in the art will envision other modifications within the scope of the claims appended hereto.

What is claimed:

1. A method of controlling a function of a surgical instrument of a surgical robot with an input of a user interface, the method comprising:
    selecting a function of the surgical instrument to link an input of the user interface with the function of the surgical instrument;
    actuating the input to activate the function of the surgical instrument; and
    delinking the input from the surgical instrument in response to an event of the surgical robot or the user interface.

2. The method according to claim 1, wherein selecting a function of the surgical instrument includes actuating a selection control of the user interface to a desired position.

3. The method according to claim 2, wherein the selection control is disposed on an input handle of the user interface.

4. The method according to claim 2, wherein actuating the selection control of the user interface to a desired position includes rotating the selection control to the desired position.

5. The method according to claim 4, wherein the desired position is one of cut, bipolar, or seal.

6. The method according to claim 2, further comprising de-assigning the input handle from a linkage that supports the surgical instrument to delink the input from the surgical instrument.

7. The method according to claim 2, wherein delinking the input from the surgical instrument includes automatically resetting the selection control to an unactuated position.

8. The method according to claim 1, further comprising decoupling the surgical instrument from a linkage of the surgical robot which affects delinking the input from the surgical instrument.

9. The method according to claim 1, wherein delinking the input from the surgical instrument occurs after a first predetermined amount of time elapses after selecting a function of the surgical instrument.

10. The method according to claim 9, further comprising resetting the first predetermined amount of time after each actuation of the input.

11. The method according to claim 10, further comprising delinking the input from the surgical instrument after a second predetermined amount of time elapses after an actuation of the input; and resetting the second predetermined amount of time after each actuation of the input.

12. The method according to claim 9, wherein the first predetermined amount of time is in a range of about 10 seconds to about 60 seconds.

13. The method according to claim 11, wherein the first and second predetermined amounts of time are different from one another.

14. The method according to claim 11, wherein the second predetermined amount of time is in a range of about 10 seconds to about 60 seconds.

15. An input handle for a user interface of a robotic surgical system, the input handle comprising:
    a body; and
    a selection control disposed on the body for linking a function of a surgical instrument associated with a linkage of a robot arm assigned to the input handle to an input, wherein the selection control is configured to reset to an unactuated position in response to an event of the robotic surgical system.

16. The input handle according to claim 15, wherein the selection control includes a null position and at least one of a cut position, a bipolar position, and a seal position.

17. The input handle according to claim 16, wherein the selection control is biased to the null position.

18. The input handle according to claim 15, wherein the selection control provides visual indicia when an input is linked to the input handle to control a function of a surgical instrument associated with a linkage of a robot arm.

19. The input handle according to claim 18, wherein the selection control is backlit to provide visual indicia when an input is linked to the input handle to control a function of a surgical instrument associated with a linkage of a robot arm.

20. The input handle according to claim 19, wherein the selection control is backlit in green when a input is linked to the input handle to control a function of a surgical instrument associated with a linkage of a robot arm, and wherein the selection control is backlit in red when a input is not linked to the input handle to control a function of a surgical instrument associated with a linkage of a robot arm.

* * * * *